(12) United States Patent
Jensen

(10) Patent No.: US 7,603,155 B2
(45) Date of Patent: Oct. 13, 2009

(54) METHOD AND SYSTEM OF ACQUIRING IMAGES WITH A MEDICAL IMAGING DEVICE

(75) Inventor: Vernon Thomas Jensen, Draper, UT (US)

(73) Assignee: General Electric Company, Schenectady, NY (US)

( * ) Notice: Subject to any disclaimer, the term of this patent is extended or adjusted under 35 U.S.C. 154(b) by 678 days.

(21) Appl. No.: 11/135,908

(22) Filed: May 24, 2005

(65) Prior Publication Data

US 2006/0293582 A1   Dec. 28, 2006

(51) Int. Cl.
*A61B 5/05* (2006.01)
*H05G 1/60* (2006.01)
*A61B 6/08* (2006.01)

(52) U.S. Cl. .............. 600/407; 600/424; 378/20; 378/205

(58) Field of Classification Search ............... 600/424, 600/426, 407, 437; 378/20, 205; 382/107, 382/284, 287; 345/672
See application file for complete search history.

(56) References Cited

U.S. PATENT DOCUMENTS

| | | | |
|---|---|---|---|
| 5,671,739 A | | 9/1997 | Darrow et al. |
| 6,666,579 B2* | | 12/2003 | Jensen ............... 378/197 |
| 6,674,879 B1* | | 1/2004 | Weisman et al. .......... 382/128 |
| 6,764,217 B2* | | 7/2004 | Yasuda et al. ............ 378/205 |
| 6,947,786 B2* | | 9/2005 | Simon et al. ............. 600/427 |
| 7,072,501 B2* | | 7/2006 | Wood et al. .............. 382/132 |
| 2002/0154801 A1 | | 10/2002 | Ohishi |
| 2004/0073111 A1* | | 4/2004 | Poland et al. ............ 600/437 |

OTHER PUBLICATIONS

International Search Report from GB0610097.8; Aug. 31, 2006.

* cited by examiner

*Primary Examiner*—Eric F Winakur
*Assistant Examiner*—Katherine L Fernandez
(74) *Attorney, Agent, or Firm*—McAndrews, Held & Malloy, Ltd.; Peter J. Vogel; Michael A. Dellapenna

(57) ABSTRACT

Methods and systems of acquiring images with a medical imaging device are provided. The method includes tracking a region of interest (ROI) location through a tracking system. Further, the method includes acquiring a first image of an object with the medical imaging device. In addition, the method includes indicating a virtual ROI location on the first image that corresponds to the ROI location. Further, the method includes moving the medical imaging device and determining the movement of the ROI location through the tracking system. The medical imaging system is moved, in order to acquire another image from a perspective that is different from that of the first image. In addition, the method includes correlating the movement of the ROI location with a shift of the virtual ROI location on the first image. Furthermore, the method includes shifting the virtual ROI location on the first image according to the correlation of the movement of the ROI location.

41 Claims, 6 Drawing Sheets

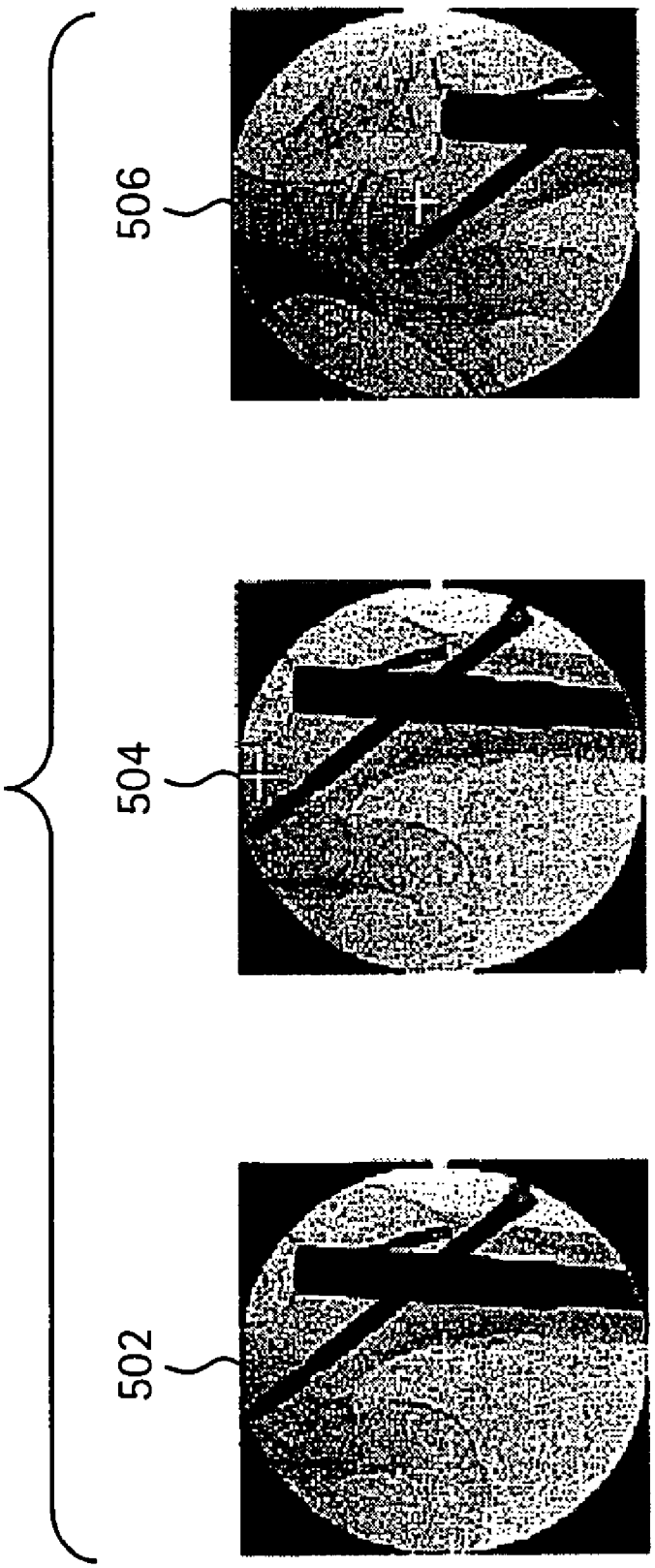

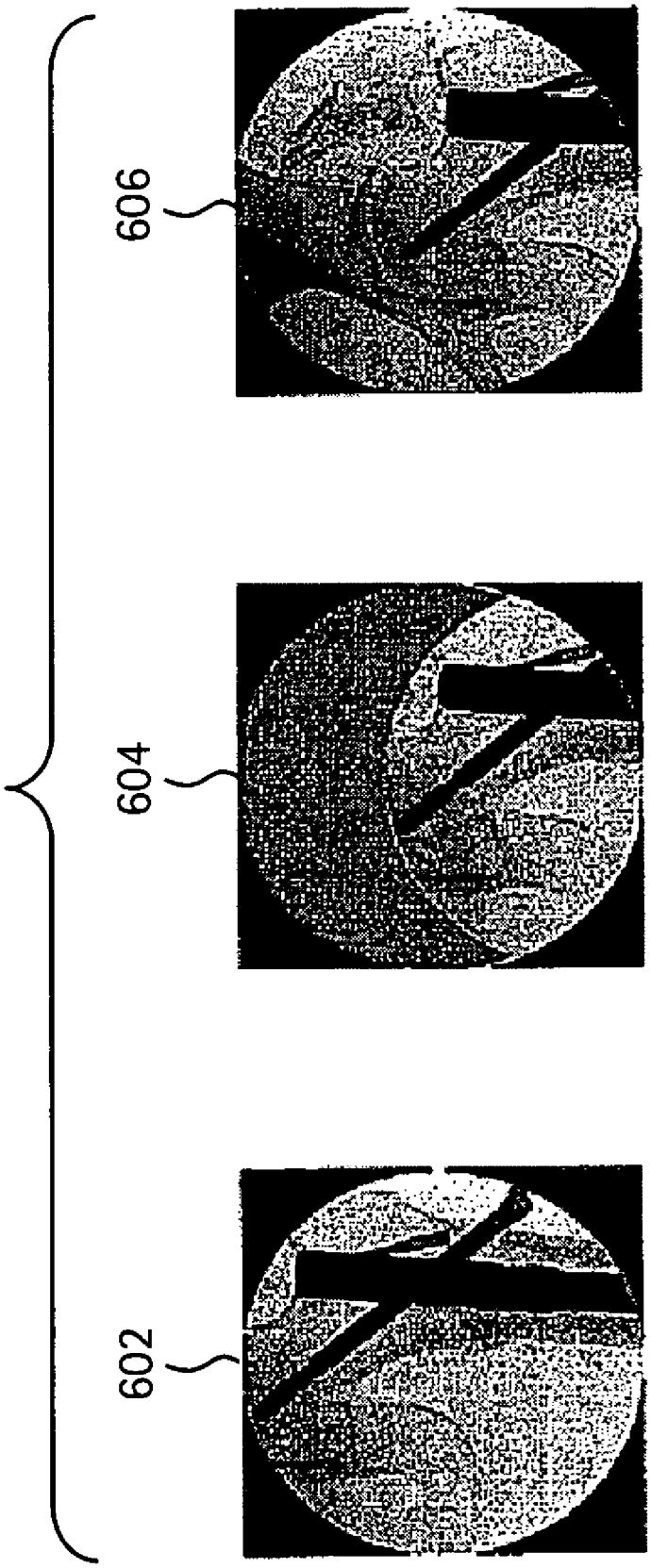

METHOD AND SYSTEM OF ACQUIRING IMAGES WITH A MEDICAL IMAGING DEVICE

BACKGROUND OF THE INVENTION

Embodiments of the present invention generally relate to medical imaging devices, and more particularly, to methods and systems of acquiring images with medical imaging devices.

Medical imaging techniques, including X-ray, Computerized Axial Tomography (CAT), and ultrasound are well established. With these techniques, an examining physician is provided with high resolution images that assist the examining physician to perform subsequent detailed study and diagnosis.

Additionally, surgical navigation systems are used to track the location of a medical instrument within an operating environment. Such systems provide pre-operative images for improving intra-operative visualization of an anatomical structure of a patient. Intra-operative image data acquisition enables determination of a precise spatial correlation between an image data and the anatomical structure of the patient.

For example, identifiable landmarks may be formed on, or attached to, a fluoroscopic C-arm, and to the patient, or a frame, or a table on which the patient is positioned. These identifiable landmarks are typically visible in the images. Further, these identifiable landmarks are typically clearly identifiable and registered to the patient. Fiducial landmarks may be attached to the patient a day prior to surgery, to enable CT measurements for planning and intra-operative navigation purposes. During the surgery, the landmark points are identified in the images, and at least three pairs of the corresponding points are localized on the patient for subsequent use with the help of a navigation system. The co-ordinate transformation between the image data and the patient is determined from the corresponding pairs of points, which are usually at least three.

In known medical imaging devices, it is difficult to accurately position the medical imaging device at the center of the anatomy of interest without the use of continuous X-rays or multiple X-ray exposures. Further, the image may be rotated in an orientation in a manner that is different from the orientation at which the examining physician is attempting to perform the surgery. Some known medical imaging devices use integrated or add-on laser aiming devices to minimize the amount of X-ray exposure that is required to achieve the desired anatomical position. These known medical imaging devices only indicate target surfaces, and do not predict the precise alignment of the patient and the C-arm. Further, these known medical imaging devices employ X-ray radiation, which is known to have an accumulative negative effect on human health.

BRIEF DESCRIPTION OF THE INVENTION

In one exemplary embodiment, a method of acquiring images with a medical imaging device is provided. The method includes tracking a region of interest (ROI) location through a tracking system. Further, the method includes acquiring a first image of an object with the medical imaging device. In addition, the method includes indicating a virtual ROI location on the first image that corresponds to the ROI location. Further, the method includes moving the medical imaging device and determining the movement of the ROI location through the tracking system. The medical imaging system is moved, in order to acquire another image from a perspective that is different from that of the first image. In addition, the method includes correlating the movement of the ROI location with a shift of the virtual ROI location on the first image. Furthermore, the method includes shifting the virtual ROI location on the first image according to the correlation of the movement of the ROI location.

In another exemplary embodiment, a medical imaging system is provided. The medical imaging system includes a medical imaging device. The medical imaging device is adapted to acquire an image of an object. The medical imaging system further includes a navigation subsystem that is configured to track the ROI location of the medical imaging device. Further, the medical imaging system includes an imaging control subsystem that communicates with the medical imaging device and the navigation subsystem. The imaging control subsystem includes a display unit. The imaging control subsystem is configured to display the image on the display unit. Further, the imaging control subsystem is configured to display a graphical representation of the ROI location on the image. The imaging control subsystem moves the graphical representation of the ROI location over the image, based on tracking data that is received by the navigation subsystem.

BRIEF DESCRIPTION OF THE DRAWINGS

FIG. 5 shows images that illustrate the effect of applying the methods of acquiring images with a medical imaging device, in accordance with an exemplary embodiment of the present invention.

FIG. 6 shows images that illustrate the effect of applying the methods of acquiring images with a medical imaging device, in accordance with another exemplary embodiment of the present invention.

Figure 1:
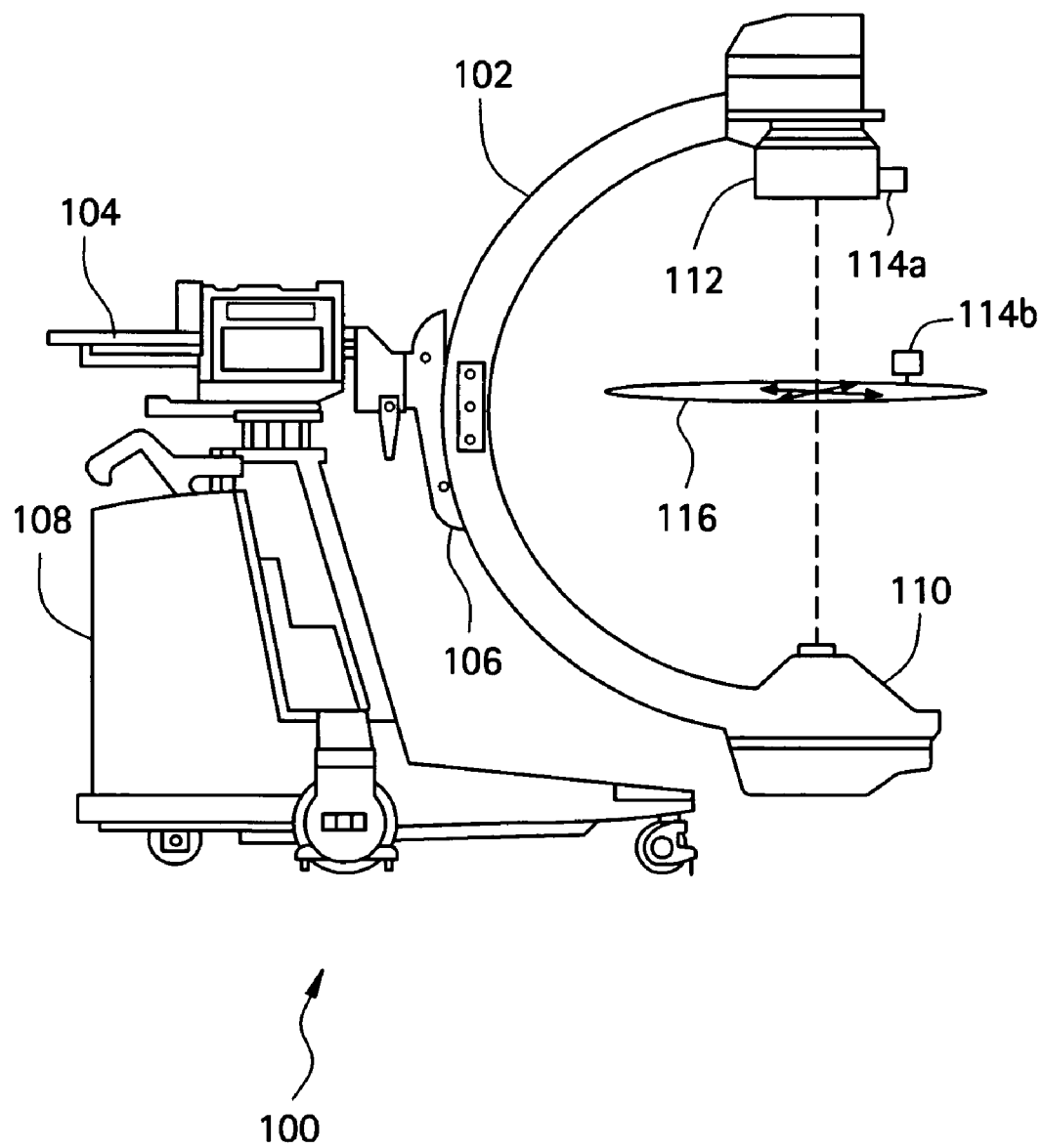
FIG. 1 illustrates an X-ray C-arm system, in which various embodiments of the present invention may be implemented.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

DETAILED DESCRIPTION OF THE INVENTION

Various embodiments of the present invention provide methods and systems of acquiring images with a medical imaging device. The medical imaging device may be a fluoroscopic imaging device such as an X-ray C-arm system, an ultrasound imaging system, a single photon emission computed tomography (SPECT) system, a computed tomography (CT) system, an optical coherence tomography (OCT) system, a positron emission tomography (PET) imaging system, and the like.

For example, embodiments of the present invention may be used with an X-ray C-arm having an X-ray source positioned on one distal end of the arm, with a detector positioned on the other distal end of the arm, such as shown and described in U.S. Pat. No. 6,104,780, entitled "Mobile bi-planar fluoroscopic imaging apparatus," U.S. Pat. No. 5,802,719, entitled "One piece C-arm for X-ray diagnostic equipment," and U.S. Pat. No. 5,627,873, entitled "Mini C-arm assembly for mobile X-ray imaging system," all of which are hereby incorporated by reference in their entireties. Optionally, the imaging system may be an MR system, such as described in U.S. Pat. No. 6,462,544, entitled "Magnetic resonance imaging apparatus," which is also hereby incorporated by reference in its entirety.

Additionally, embodiments of the present invention may also be used with Positron Emission Tomography (PET), such as shown and described in U.S. Pat. No. 6,337,481, entitled "Data binning method and apparatus for PET tomography including remote services over a network," which is hereby incorporated by reference in its entirety, Single Photon Emission Computed Tomography (SPECT), such as shown and described in U.S. Pat. No. 6,194,725, entitled "SPECT system with reduced radius detectors," which is hereby incorporated by reference in its entirety, Electron Beam Tomography (EBT), such as shown and described in U.S. Pat. No. 5,442,673, entitled "Fixed septum collimator for electron beam tomography," which is hereby incorporated by reference in its entirety, and various other imaging systems.

Embodiments of the present invention may also be used with such navigation and tracking systems as those described in U.S. Pat. No. 5,803,089, entitled "Position Tracking and Imaging System for Use in Medical Applications," which is hereby incorporated by reference in its entirety.

FIG. 1 illustrates an X-ray C-arm system 100, in which various embodiments of the present invention may be implemented. X-ray C-arm system 100 includes a C-arm 102. C-arm 102 has inner and outer circumferences. C-arm 102 has a uniformly circular C-shape, and may alternatively comprise any arc-shaped member. C-arm 102 is held in a suspended position by support member 104 such as a structure that includes a support arm 106. Support arm 106 is mounted on a wheeled base 108 and enables rotational movement of the C-arm by means such as a bearing assembly. The bearing assembly is configured between support arm 106 and C-arm 102, the support itself being rotatably mounted with respect to wheeled base 108, and so forth. X-ray C-arm system 100 further includes an X-ray source 110 and an image receptor 112. In an embodiment of the present invention, image receptor 112 may be an image intensifier, or the like. Image receptor 112 includes a camera assembly. X-ray source 110 and image receptor 112 are mounted on opposing locations, respectively, on C-arm 102. A high-voltage cable assembly supplies power to X-ray source 110 and image receptor 112. X-ray C-arm system 100 further includes tracking elements 114a and 114b. Tracking element 114 a is affixed to image receptor 112. Tracking element 114b is secured to a frame or a table of reference 116 on which a patient to be examined is positioned. Tracking element 114b may have a rigid or oriented housing, so that when tracking element 114b is affixed to table of reference 116, the tracked co-ordinates of tracking element 114b may yield all the co-ordinates with only a defined constant offset of table of reference 116. To produce or detect a field that is modulated in phase, frequency or time, tracking element 114b may be energized as a field generator or sampled as a field sensor, and so forth. Therefore, some or all of the x-, y-, z-, roll-, pitch-, and yaw co-ordinates of tracking element 114b and table of reference 116 are quickly and accurately determined. Various methods for determining x-, y-, z-, roll-, pitch-, and yaw co-ordinates are known.

In various embodiments of the present invention, tracking element 114b may belong to a tracking system. Examples of a tracking system include a light-emitting diode (LED) tracking system, an optical tracking system, an ultrasound-based tracking system, an inertial position tracking system, and an acoustic-based tracking system. For example, in an embodiment of the present invention, tracking element 114b may be a collection of LEDs that are positioned at table of reference 116. The positions of the LEDs on table of reference 116 are detected by means of a stereo charge-coupled device (CCD) camera system. In an embodiment of the present invention, tracking element 114b may employ a magnetic field element, which otherwise operates mainly as a point-origin field generator or field sensor. The magnetic field element may be configured with three mutually orthogonal coils.

A patient is supported on table of reference 116 that is positioned between image receptor 112 and X-ray source 110. An X-ray beam passes through an object to be imaged, such as a patient's spine or knee. The location where the X-ray beam passes the object to be imaged is the region of interest (ROI) location.

Figure 2:
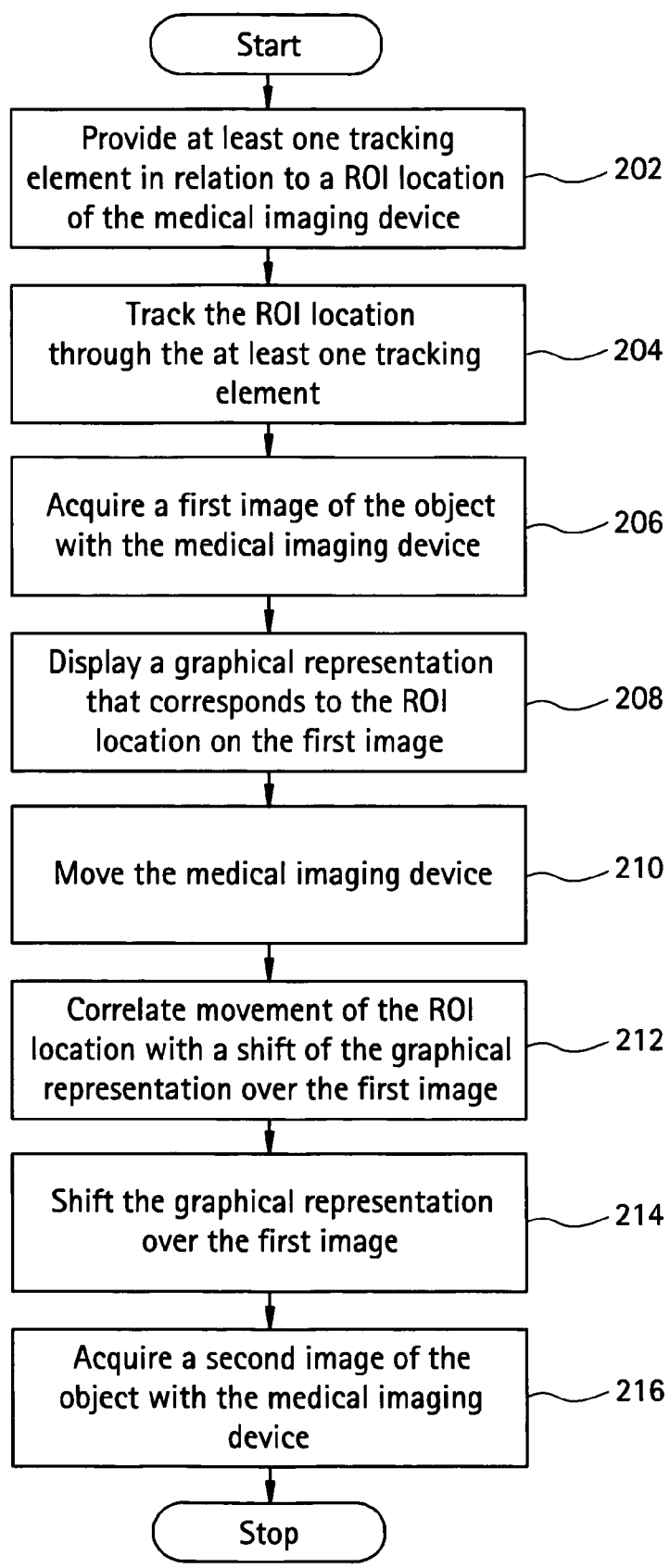
FIG. 2 is a flowchart illustrating a method of acquiring images with a medical imaging device, in accordance with an embodiment of the present invention.

FIG. 2 is a flowchart illustrating a method of acquiring images with a medical imaging device, in accordance with an exemplary embodiment of the present invention. At 202, at least one tracking element in relation to a region of interest (ROI) location of the medical imaging device is provided. The ROI location refers to the location in which an object to be imaged is placed. The X-ray beam passes through the ROI location. As such, an object to be imaged is positioned within the ROI location for imaging. The object may be a heart, a vertebra, an aorta, a liver, a lung, and so forth. The ROI is located between the X-ray source and the detector. An X-ray beam that is emitted from an X-ray source includes an imaging area. The ROI location coincides with the imaging area. In an exemplary embodiment of the present invention, tracking elements such as receiver and transmitter coil trios, and so forth, may be affixed, mounted or positioned directly to the medical imaging device. In an embodiment of the present invention, the tracking elements may be secured to an anatomical structure of a patient that is being imaged. In another embodiment of the present invention, the tracking elements may also be secured to a frame or a table on which the patient is positioned.

At 204, the ROI location is tracked through the tracking elements. The tracking elements may belong to one of a light emitting diode (LED) tracking system, an optical tracking system, an electromagnetic tracking system, an ultrasound-based tracking system, an inertial position tracking system, and an acoustic-based tracking system.

At 206, a first image of the object is acquired with the medical imaging device by emitting a plurality of X-rays from the X-ray source through the ROI location. In an embodiment of the present invention, wherein the medical imaging device is an ultrasound imaging system, the first image is acquired by emitting a plurality of ultrasound waves from the source, through the ROI location.

At 208, a graphical representation that corresponds to the ROI location is displayed on the first image. Examples of the graphical representation include a crosshair, an arrow, brackets, a circle, a square, and any two-dimensional figure that encloses an open central figure. In an embodiment of the present invention, the graphical representation may be located at the center of the first image. In another embodiment of the present invention, the graphical representation may be located around the first image. For example, the graphical representation may be a masking frame that corresponds to the ROI location and is located around the first image.

At 210, the medical imaging device is moved, so as to acquire another image from a perspective that is different from that of the first image. During the movement of the medical imaging device, the movement of the ROI location is determined through the tracking elements. In an embodiment of the present invention, the medical imaging device is an X-ray C-arm system, and rotating the C-arm of the X-ray C-arm system may move the medical imaging device. The movement of the medical imaging device results in the movement of the ROI location. The movement of the ROI location is tracked through the tracking elements.

At 212, the movement of the ROI location, which takes place due to the movement of the medical imaging device, is correlated with a shift of the graphical representation over the first image. At 214, the graphical representation is shifted over the first image. In an embodiment of the present invention, the graphical representation is a masking frame, and shifting of the masking frame refers to masking portions of the first image with the masking frame. At 216, a second image of the object is acquired with the medical imaging device. Upon acquisition of the second image, the graphical representation is reset at the second image. The graphical representation may be reset at the center of the second image, or around the second image. The second image of the object is acquired by emitting a plurality of X-rays from the X-ray source, through the ROI location. In an embodiment of the present invention, the medical imaging device is an ultrasound imaging system, and the second image is acquired by emitting a plurality of ultrasound waves from the source through the ROI location.

Figure 3:
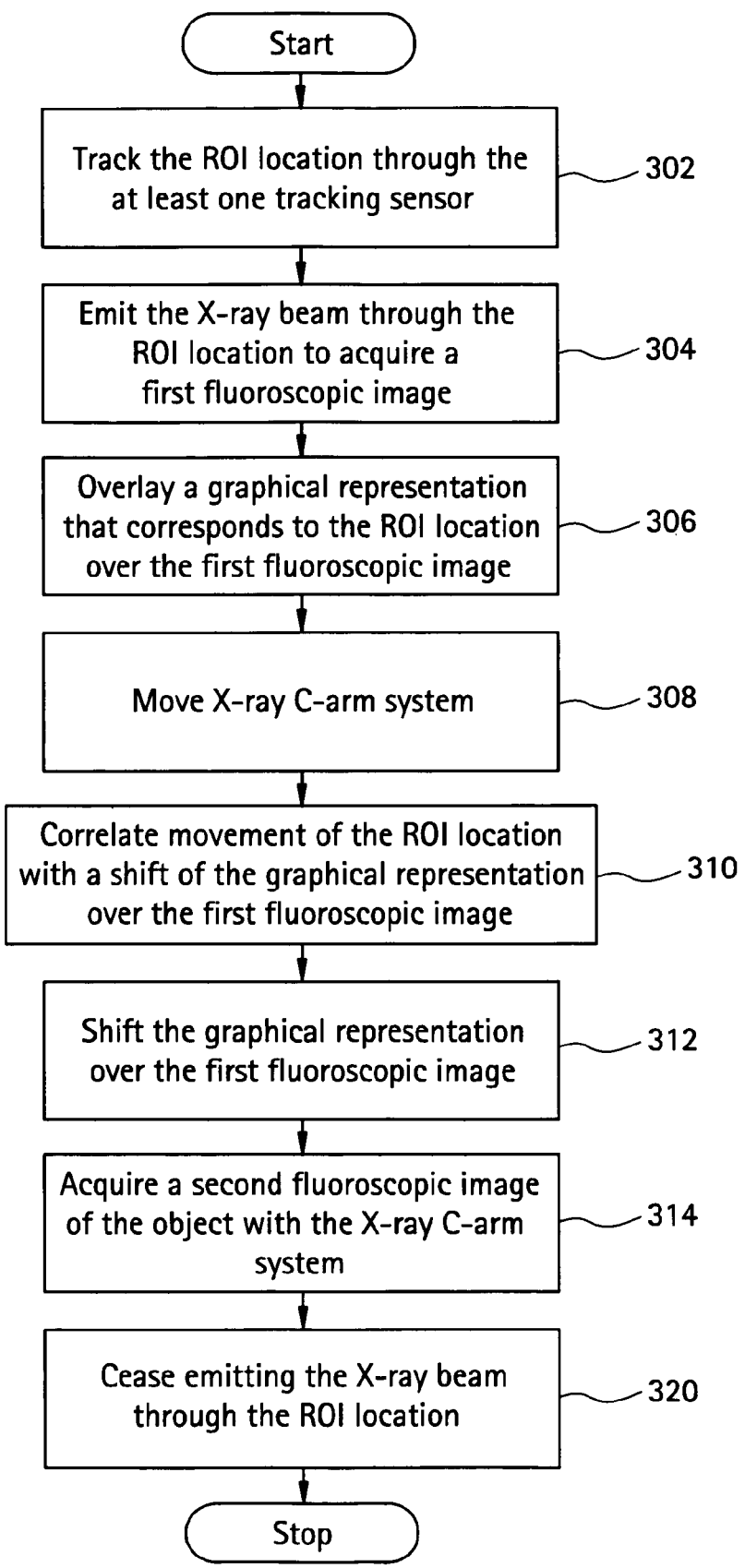
FIG. 3 is a flowchart illustrating a method of acquiring images with an X-ray C-arm system, in accordance with another embodiment of the present invention.

FIG. 3 is a flowchart illustrating a method of acquiring images with X-ray C-arm system 100, in accordance with an exemplary embodiment of the present invention.

At 302, the ROI location is tracked through at least one of the tracking sensors by receiving signals from at least one of the transmitters that are provided in relation to the ROI location. The signals may be one of ultrasonic, inertial position, optical, electromagnetic and acoustic.

At 304, an X-ray beam is emitted through the ROI location, to acquire a first fluoroscopic image of the object. At 306, a graphical representation that corresponds to the ROI location is overlaid over the first fluoroscopic image. In an embodiment of the present invention, the graphical representation may be located at a centre of the first fluoroscopic image. In another embodiment of the present invention, the graphical representation may be located around the first fluoroscopic image. For example, the graphical representation may be a masking frame that corresponds to the ROI location and is overlaid around the first fluoroscopic image.

At 308, X-ray C-arm system 100 is moved so as to acquire another image from a perspective that is different from that of the first image. During the movement of the medical imaging device, the movement of the ROI location is determined through at least one of the tracking sensors. X-ray C-arm system 100 may be moved by rotating C-arm 102. The movement of X-ray C-arm system 100 leads to the movement of the ROI location.

At 310, the movement of the ROI location that takes place due to the movement of X-ray C-arm system 100 is correlated with a shift of the graphical representation, which represents a virtual ROI location, over the first fluoroscopic image. At 312, the graphical representation is shifted over the first fluoroscopic image. In an embodiment of the present invention, wherein the graphical representation is a masking frame, portions of the first fluoroscopic image are masked with the masking frame.

At 314, a second fluoroscopic image of the object is acquired with X-ray C-arm system 100. The graphical representation is reset at the second fluoroscopic image. In an embodiment of the present invention, the graphical representation is reset at the center of the second fluoroscopic image. In another embodiment of the present invention, the graphical representation is reset around the second fluoroscopic image. The second fluoroscopic image of the object is acquired by emitting the X-ray beam through the ROI location. At 316, the emission of the X-ray beam through the ROI location, which is performed during the movement of X-ray C-arm system 100, is ceased.

Figure 4:
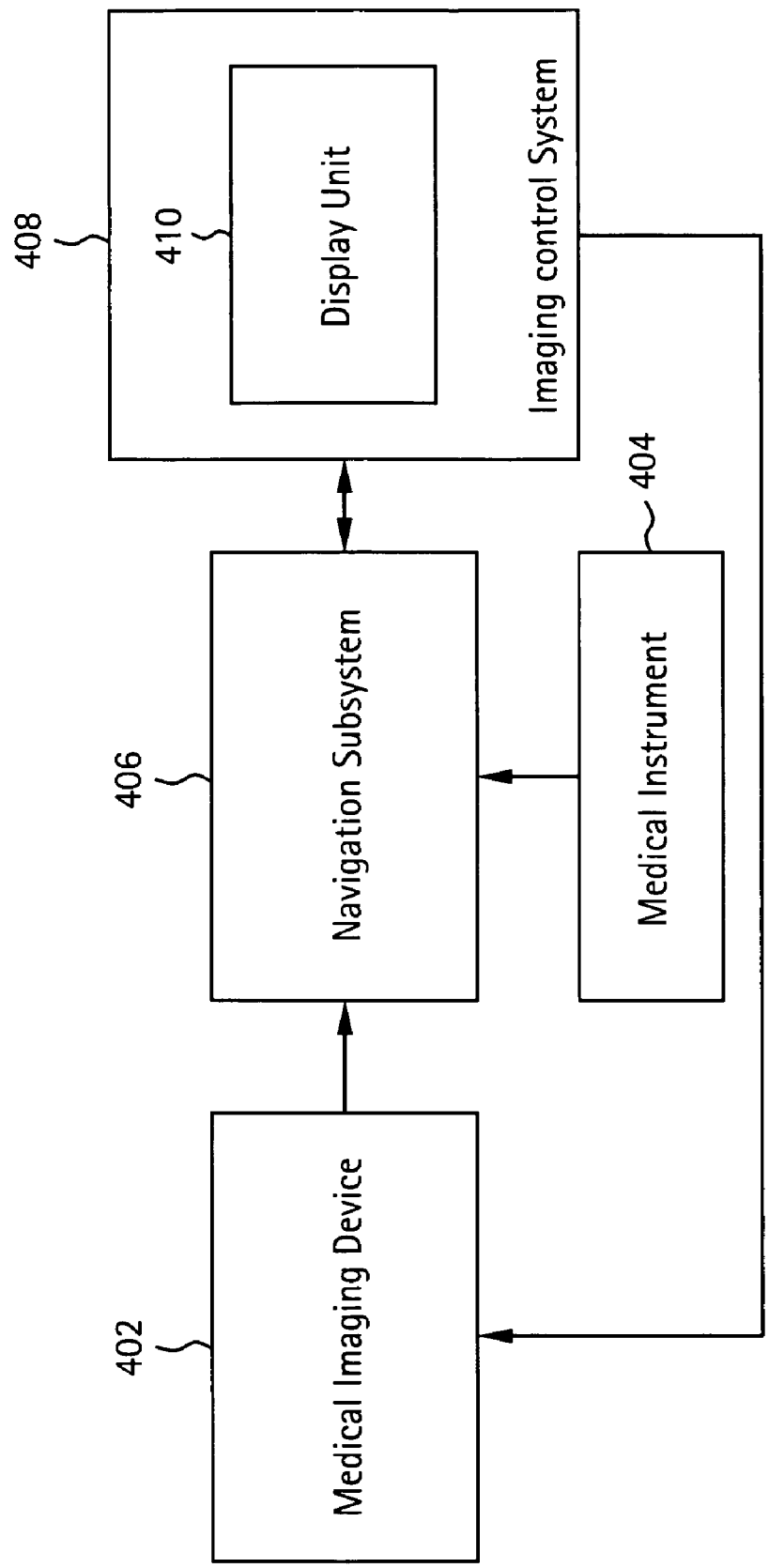
FIG. 4 illustrates a block diagram of a medical imaging system, in accordance with an exemplary embodiment of the present invention.

FIG. 4 illustrates a block diagram of a medical imaging system 400, in accordance with an exemplary embodiment of the present invention. Medical imaging system 400 includes a medical imaging device 402, a medical instrument 404, a navigation subsystem 406, and an imaging control subsystem 408. Medical imaging device 402 is configured to acquire an image of the object. The image may be a single instantaneous image, that is, an image taken at a precise instant in time. Further, medical imaging device 402 is configured to cease image acquisition during the movement of medical imaging device 402. In an embodiment, medical imaging device 402 may be a fluoroscopic C-arm, which includes a source and a detector. The ROI is located between the source and the detector.

Medical imaging system 400 includes medical instrument 404. Medical instrument 404 is separate and distinct from medical imaging device 402. Examples of medical instrument 404 include an orthopedic drill, a catheter, an awl, a reamer, a scalpel, a scope, a stent, a probe, a screwdriver, and so forth.

Medical imaging system 400 includes navigation subsystem 406. Navigation subsystem 406 is configured to track the ROI location of medical imaging device 402. Navigation subsystem 406 assists in generating a positional relationship between the patient and the image, and therefore produces a direct spatial correlation between patients' images and their anatomy. Examples of navigation subsystem 406 include an optical tracking system, a LED tracking system, an electromagnetic tracking system, an ultrasound-based tracking system, an inertial position tracking system, and an acoustic-based tracking system.

Imaging control subsystem 408 includes a display unit 410. Imaging control subsystem 408 is configured to display the image on display unit 410. Further, imaging control subsystem 408 is configured to display the graphical representation of the ROI location on the image. Imaging control subsystem 408 moves the graphical representation of the ROI location over the image. The movement of the graphical representation of the ROI location is based on the tracking data that is received by navigation subsystem 406. In an embodiment of the present invention, imaging control subsystem 408 moves the graphical representation of the ROI location over a single instantaneous image. Furthermore, imaging control subsystem 408 is configured to reset the location of the graphical representation of the ROI location when medical imaging device 402 acquires an additional image of the object. Imaging control subsystem 408 communicates with medical imaging device 402 and navigation subsystem 406, to perform the functions described above.

FIG. 5 shows images to illustrate the effects of applying the methods of acquiring images with a medical imaging device, in accordance with an exemplary embodiment of the present invention. Image 502 shows a crosshair that is displayed at the center of a first image. Image 504 shows the crosshair that has been shifted over the first image to a new position, which indicates the current ROI location of the medical imaging device. The crosshair has been shifted due to the movement of the medical imaging device. Image 506 shows the crosshair that has been reset at the new center of a second image.

FIG. 6 shows images, to illustrate the effect of applying the methods of acquiring images with a medical imaging device, in accordance with another exemplary embodiment of the present invention. Image 602 shows a first image acquired by the medical imaging device. Image 604 shows a portion of the first image that has been masked by a masking frame due to the fact that the ROI location of the medical imaging device has shifted downward. Image 606 shows a second image that has been acquired after resetting the masking frame.

The various embodiments of the present invention provide a medical imaging system that improves the flow of surgical procedures by reducing the time of operating the medical imaging device. Further, the various embodiments of the present invention provide a medical imaging system that improves the accuracy of positioning the C-arm. Furthermore, the various embodiments of the present invention provide a medical imaging system that employs a lower dose of X-ray radiation, since positioning of the medical imaging device is performed without the use of continuous fluoroscopy.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

What is claimed is:

1. A method of acquiring images with a fluoroscopic imaging device, wherein the fluoroscopic imaging device includes a region of interest (ROI) location in which an object to be imaged is positioned, the method comprising:
    providing tracking elements in relation to the ROI location of the fluoroscopic imaging device;
    tracking the ROI location through the tracking elements;
    acquiring a first image of the object with the fluoroscopic imaging device, wherein said acquiring the first image comprises emitting a plurality of X-rays from a source through the ROI location;
    displaying a graphical representation that corresponds to the ROI location on the first image;
    moving the fluoroscopic imaging device, wherein movement of the ROI location during said moving is determined through said tracking;
    correlating movement of the ROI location during said moving with a shift of the graphical representation over the first image;
    shifting the graphical representation over the first image according to said correlating; and
    acquiring a second image of the object with the fluoroscopic imaging device, wherein said acquiring the second image comprises emitting a plurality of X-rays from the source through the ROI location.

2. The method of claim 1, wherein said displaying comprises locating the graphical representation at a center of the first image prior to said moving.

3. The method of claim 2, wherein said acquiring a second image comprises resetting the graphical representation at a center of the second image.

4. The method of claim 2, wherein said acquiring a second image comprises resetting the graphical representation around the second image.

5. The method of claim 1, wherein said displaying comprises locating the graphical representation around the first image prior to said moving.

6. The method of claim 1, further comprising ceasing image acquisition of the fluoroscopic imaging device during said moving.

7. The method of claim 1, wherein the fluoroscopic imaging device is a C-arm having the source at one end and a detector at another end, wherein the ROI location is located between the source and the detector, and wherein said moving comprises rotating the C-arm.

8. The method of claim 1, wherein the graphical representation is at least one of an arrow, crosshairs, brackets, and two-dimensional figure enclosing an open central area.

9. The method of claim 1, wherein the graphical representation comprises a masking frame, wherein said displaying comprises displaying the masking frame around the first image, and wherein said shifting comprises masking portions of the first image with the masking frame.

10. The method of claim 1, wherein said tracking comprises tracking the ROI location through the tracking elements by one of an ultrasound, an inertial position, an optical and an electromagnetic tracking system.

11. The method of claim 1, wherein said providing comprises fixing at least one of the tracking elements to the fluoroscopic imaging device.

12. The method of claim 1, wherein said providing comprises securing at least one of the tracking elements to a patient being imaged.

13. A method of acquiring images with a fluoroscopic imaging device having a C-arm supporting an imaging source at one end and a detector at another end, wherein the imaging source is configured to emit an X-ray beam that impinges on the detector, wherein the X-ray beam includes an imaging area, and wherein an object to be imaged is positioned within a region of interest (ROI) location that coincides with the imaging area, the method comprising:
    providing at least one transmitter and at least one tracking sensor in relation to the ROI location;
    tracking the ROI location through the at least one tracking sensor receiving transmitted signals from the at least one transmitter;
    emitting the X-ray beam through the ROI location to acquire a first fluoroscopic image of the object;
    overlaying a graphical representation that corresponds to the ROI location over the first fluoroscopic image;
    moving the fluoroscopic imaging device in order to image the object from a different perspective, wherein movement of the ROI location during said moving is determined through said tracking;
    correlating movement of the ROI location during said moving with a shift of the graphical representation over the first fluoroscopic image;
    shifting the graphical representation over the first fluoroscopic image according to said correlating; and
    acquiring a second fluoroscopic image of the object with the fluoroscopic imaging device.

14. The method of claim 13, wherein said overlaying comprises locating the graphical representation at a center of the first fluoroscopic image prior to said moving.

15. The method of claim 14, wherein said acquiring a second fluoroscopic image comprises resetting the graphical representation at a center of the second fluoroscopic image.

16. The method of claim 14, wherein said acquiring a second fluoroscopic image comprises resetting the graphical representation around the second fluoroscopic image.

17. The method of claim 13, wherein said overlaying comprises locating the graphical representation around the first fluoroscopic image prior to said moving.

18. The method of claim 13, further comprising ceasing said emitting during said moving.

19. The method of claim 13, wherein the graphical representation is at least one of an arrow, crosshairs, brackets, and two-dimensional figure enclosing an open central area.

20. The method of claim 13, wherein the graphical representation comprises a masking frame, wherein said overlaying comprises overlaying the masking frame around the first fluoroscopic image, and wherein said shifting comprises masking portions of the first fluoroscopic image with the masking frame.

21. The method of claim 13, wherein said tracking comprises tracking the ROI location through the at least one tracking sensor receiving one of ultrasonic, inertial position, optical and electromagnetic signals from the at least one transmitter.

22. The method of claim 13, wherein said providing comprises fixing the at least one tracking sensor to the fluoroscopic imaging device.

23. The method of claim 13, wherein said providing comprises securing the at least one tracking sensor to a patient being imaged.

24. A method of acquiring images with a fluoroscopic imaging device, wherein the fluoroscopic imaging device includes a region of interest (ROI) location in which an object to be imaged is positioned, the method comprising:
tracking the ROI location through a tracking system;
acquiring a first image of the object with the fluoroscopic imaging device, wherein said acquiring the first image comprises emitting a plurality of X-rays from a source through the ROI location;
indicating a virtual ROI location on the first image that corresponds to the ROI location;
moving the fluoroscopic imaging device in order to acquire another image from a different perspective than that of the first image, wherein movement of the ROI location during said moving is determined through said tracking;
correlating movement of the ROI location during said moving with a shift of the virtual ROI location on the first image; and
shifting the virtual ROI location on the first image according to said correlating.

25. The method of claim 24, wherein said indicating a virtual ROI location comprises displaying a graphical representation that corresponds to the ROI location on the first image.

26. The method of claim 24, wherein said indicating comprises locating the virtual ROI at a center of the first image prior to said moving.

27. The method of claim 24, wherein said indicating comprises locating the virtual ROI at a center of a masking frame that surrounds the first image prior to said moving.

28. The method of claim 24, further comprising ceasing said acquiring during said moving.

29. The method of claim 24, wherein the virtual ROI is represented by at least one of an arrow, crosshairs, brackets, and two-dimensional figure enclosing an open central area.

30. The method of claim 24, wherein said shifting comprises masking portions of the first image with the masking frame.

31. The method of claim 24, wherein the tracking system is one of an ultrasound, an inertial position, an optical and an electromagnetic tracking system.

32. A medical imaging system, comprising:
a fluoroscopic imaging device comprising a source and a detector, wherein a region of interest (ROI) location is located between said source and said detector, wherein an object to be imaged is positioned within the ROI location, said fluoroscopic imaging device adapted to acquire an image of the object;
a navigation subsystem configured to track the ROI location of said fluoroscopic imaging device; and
an imaging control subsystem comprising a display unit, said imaging control subsystem being in communication with said fluoroscopic imaging device and said navigation subsystem, said imaging control subsystem operative to display (i) the image on said display unit, and (ii) a graphical representation of the ROI location on the image, wherein said imaging control subsystem moves the graphical representation of the ROI location over the image based on tracking data received by said navigation subsystem.

33. The medical imaging system of claim 32, further comprising a medical instrument that is separate and distinct from said fluoroscopic imaging device, wherein said navigation subsystem is also configured to track movement of said medical instrument.

34. The medical imaging system of claim 32, wherein the image is a single instantaneous image, and wherein said imaging control subsystem moves the graphical representation of the ROI location over the single instantaneous image.

35. The medical imaging system of claim 32, wherein said imaging control subsystem initially locates said graphical representation at a center of the image immediately after the image is acquired by said fluoroscopic imaging device.

36. The medical imaging system of claim 32, wherein said imaging control subsystem initially locates said graphical representation around a center of the image immediately after the image is acquired by said fluoroscopic imaging device.

37. The medical imaging system of claim 32, wherein said imaging control subsystem resets a location of said graphical representation when said fluoroscopic imaging device acquires an additional image.

38. The medical imaging system of claim 32, wherein said fluoroscopic imaging device ceases image acquisition when said fluoroscopic imaging device is moving.

39. The medical imaging system of claim 32, wherein the graphical representation is at least one of an arrow, crosshairs, brackets, and two-dimensional figure enclosing an open central area.

40. The medical imaging system of claim 32, wherein the graphical representation comprises a masking frame positioned around at least a portion of the image.

41. The medical imaging system of claim 32, wherein said navigation subsystem is an electromagnetic tracking system.

* * * * *

UNITED STATES PATENT AND TRADEMARK OFFICE
CERTIFICATE OF CORRECTION

PATENT NO. : 7,603,155 B2  Page 1 of 1
APPLICATION NO. : 11/135908
DATED : October 13, 2009
INVENTOR(S) : Vernon Thomas Jensen It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1060 days.

Signed and Sealed this

Fifth Day of October, 2010

David J. Kappos
*Director of the United States Patent and Trademark Office*